United States Patent [19]

Mobilio

[11] Patent Number: 5,508,302
[45] Date of Patent: Apr. 16, 1996

[54] PHOSPHOLIPASE A2 INHIBITORS

[75] Inventor: Dominic Mobilio, Franklin Park, N.J.

[73] Assignee: American Home Products Corporation, Madison, N.J.

[21] Appl. No.: 313,977

[22] Filed: Sep. 28, 1994

[51] Int. Cl.$^6$ .......................... A61K 31/38; A61K 31/34; C07D 333/16; C07D 307/26

[52] U.S. Cl. .......................... 514/445; 514/473; 514/474; 549/64; 549/65; 549/318

[58] Field of Search .................... 514/473, 445, 514/448, 472, 447, 690, 64; 549/64, 318, 72, 313, 65; 568/376, 379; 564/256

[56] References Cited

U.S. PATENT DOCUMENTS

| | | | |
|---|---|---|---|
| 2,916,417 | 12/1959 | Horrom | 514/640 |
| 4,285,942 | 8/1981 | Budai et al. | 514/640 |
| 4,473,597 | 9/1984 | Muryobayashi et al. | 514/690 |
| 4,576,962 | 3/1986 | Mattews | 514/690 |
| 4,787,749 | 12/1988 | Jacobs et al. | 549/313 |
| 4,816,487 | 3/1989 | Scheme et al. | 514/640 |
| 4,874,782 | 10/1989 | Bonjouklian et al. | 514/473 |
| 5,013,850 | 5/1991 | Lee | 549/222 |
| 5,059,611 | 10/1991 | Lee | 514/336 |
| 5,242,945 | 9/1993 | Caufield et al. | 514/473 |
| 5,346,921 | 9/1994 | Ueno | 514/690 |
| 5,366,993 | 11/1994 | Schiehser et al. | 514/445 |

FOREIGN PATENT DOCUMENTS

| | | |
|---|---|---|
| 0295056 | 12/1988 | European Pat. Off. |
| 0418655 | 3/1991 | European Pat. Off. |
| 5087757 | 7/1980 | Japan. |
| 1044338 | 9/1966 | United Kingdom. |
| 1058243 | 2/1967 | United Kingdom. |
| 1276061 | 6/1972 | United Kingdom. |
| WO9322305 | 11/1993 | WIPO. |

OTHER PUBLICATIONS

Derwent Publication 87–067659/10 corresponding to J62019582 (1987).
Nomura et al., Chem Pharm Bulletin, 34:5188 (1986).
Kataoka et al., Chemical Abstracts, 84:175144m (1976).
Omo et al., Chemical Abstracts, 81:151976w (1974).

*Primary Examiner*—Richard L. Raymond
*Assistant Examiner*—Deborah Lambkin
*Attorney, Agent, or Firm*—Arnold S. Milowsky

[57] ABSTRACT

There are disclosed compounds of the formula:

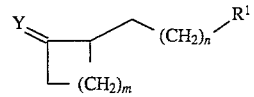

wherein $R^1$ is

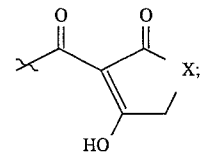

X is O, or S;

Y is O or NOR$^2$;

$R^2$ is alkyl, alkenyl, phenyl, —CH$_2$CO$_2$R$^3$, —CH$_2$Ph, —CH$_2$C$_6$F$_5$, or

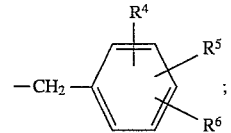

$R^3$ is hydrogen, alkyl, phenyl, or phenylalkyl;

$R^4$, $R^5$, and $R^6$ are each, independently, hydrogen, alkyl, —OH, alkoxy, —CO$_2$R$^3$, halogen, —NH$_2$, alkylamino, dialkylamino, or —NO$_2$;

m=0–20; and n=0–10 or a pharmacologically acceptable salt thereof which are useful as anti-inflammatory agents.

8 Claims, No Drawings

PHOSPHOLIPASE A2 INHIBITORS

The present invention is directed to certain phospholipase $A_2$ inhibitors and to a method for using them as anti-inflammatory agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins hag already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxidcs in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, Am. J. Pathol., 99. 743 (1980). Cyclooxygenase metabolites are known to participate directly in the inflammatory response [see Higgs et al., Annals of Clinical Research, 16, 287–299 (1984)]. This is through their vaso-depressor activities, participation in pain and fever and augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.*, 215, 115–118 (1980); *Biochem. Biophys. Res. Commun.*, 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances as mediators of inflammation and hypersensitivity is extensively reviewed in Bailey and Casey, *Ann., Reports Med. Chem.*, 17, 203–217 (1982).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkyl-arachidonylglycerophosphatidylcholine is acted upon by the $PLA_2$ the generation of platelet activating factor (PAF) is initiated; PAF is pro-inflammatory in its own fight [see Wedmore et al., *Br. J. Pharmacol.*, 74, 916–917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci., U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem, J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Throm. Res.*, 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation, as well as in the modulation of PAF-mediated biological processes, such as embryonic implantation, thus making the compounds useful as anti-fertility agents.

This invention provides compounds having the formula

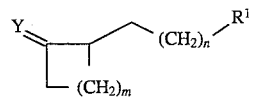

wherein
$R^1$ i

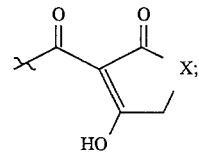

X is O, or S;

Y is O or $NOR^2$;

$R^2$ is alkyl of 1-6 carbon atoms, alkenyl of 2-7 carbon atoms, phenyl, —$CH_2CO_2R_3$, —$CH_2Ph$, —$CH_2C_6F_5$, or

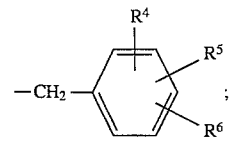

$R^3$ is hydrogen, alkyl of 1-6 carbon atoms, phenyl, or phenylalkyl of 7-12 carbon atoms;

$R^4$, $R^5$, and $R^6$ are each, independently, hydrogen, alkyl of 1-6 carbon atoms, —OH, alkoxy of 1-6 carbon atoms, —$CO_2R^3$, halogen, —$NH_2$, alkylamino of 1-6 carbon atoms, dialkylamino of 2-12 carbon atoms, or —$NO_2$;

m=0-20; and n=0-10 or a pharmacologically acceptable salt thereof.

The compounds of this invention possess antiinflammatory activity and inhibit phospholipase $A_2$ ($PLA_2$) in vitro and as such are useful in the treatment and prevention of inflammatory disease states such allergic rhinitis, allergic bronchial asthma, chronic obstructive pulmonary disease, emphysema, acute respiratory distress syndrome, and other naso-bronchial obstructive air-passageway conditions; immediate hypersensitivity maclions, such as allergic conjunctivitis; inflammatory conditions such as those present in rheumatoid arthritis, osteoarthritis, tendonitis, bursitis, psoriasis, dermatitis, eczema, seborrhea, and related skin disorders; inflammatory bowel diseases, such as Crohn's Disease, irritable bowel syndrome, and the like; and uveitis. The compounds also possess utility in the modulation of biological processes which are effected by platelet activating factor (PAF) such as embryonic implantation and as such are useful as anti-fertility agents.

The terms alkyl, alkenyl, alkoxy, aminoalkyl, dialkylamino, include both straight chain as well as branched carbon chains. The term "halo" refers to fluoro, chloro, bromo, or iodo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, iraconic and benzenesylfonic. The compounds of the invention are capable of forming alkali metal and alkaline earth salts and salts of pharmacologically acceptable cations derived from ammonia or a basic amine. Examples of the latter include but are not limited to cations such as ammonium, mono-, di-, and trimethylammonium, mono-, di-, and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonethanolammonium, and the like.

The compounds within the scope or the invention by virtue of their configuration, exhibit stereoisomerism. Accordingly, the compounds of the invention include the diastereomers, enantiomorphs, racemates and mixtures thereof.

Of the compounds of this invention, it is preferred that $m=7-12$ and $n=0-2$.

The compounds within the scope of the invention can be prepared by a variety of synthetic routes using conventional methodology. For example, the compounds of this invention in which $Y=O$, can be prepared according to the following scheme from the requisite carboxylic acids that are either commercially available or can prepared by methods described in the literature.

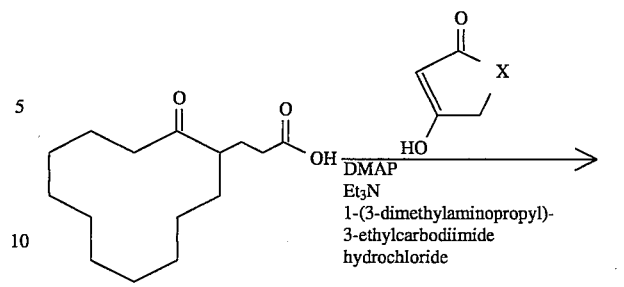

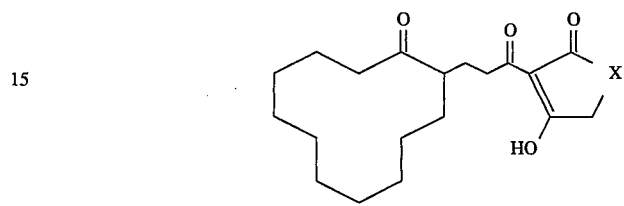

Compounds of this invention in which $Y=NOR_2$, can be prepared as outlined below. Acid I can be esterified using standard literature procedures affording II. The ester can then be converted to the oxime III by treatment with the requisite commercially available or synthetically prepared O-substituted hydroxyl amine or a salt thereof. The oxime-ester can then be hydrolyzed to IV that can be coupled with intronic acid or thiotetronic acid affording the final product V.

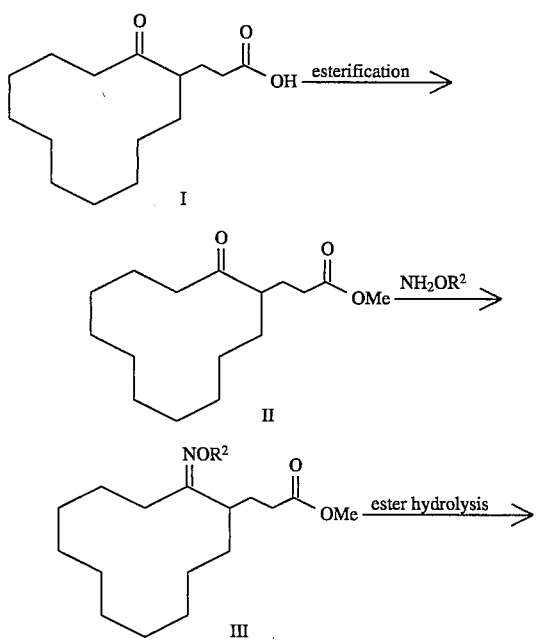

-continued

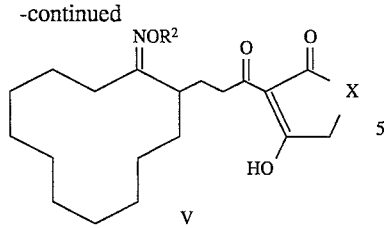

The compounds of the invention, by virtue of their ability to inhibit activity of $PLA_2$ enzyme, are useful in the treatment of conditions mediated by products of the oxidation of arachidonic acid. Accordingly, the compounds are useful as antiinflammatory agents that are indicated in the prevention and treatment of such conditions as allergic rhinitis, allergic bronchial asthma, chronic obstructive pulmonary disease, emphysema, acute respiratory distress syndrome, and other naso-bronchial obstructive air-passageway conditions; immediate hypersensitivity reactions, such as allergic conjunctivitis; inflammatory conditions such as those present in rheumatoid arthritis, osteoarthritis, tendonitis, bursitis, psoriasis, dermatitis, eczema, seborrhea, and related skin disorders; inflammatory bowel diseases, such as Crohn's Disease, irritable bowel syndrome, and the like; and uveitis.

When used as antiinflammatory agents, the compounds of this invention can be administered orally, parenterally, intranasally, intrabronchially, transdermally, rectally, or vaginally. The compounds of this invention can be formulated neat or with a pharmaceutical carrier to a mammal in need thereof.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such ms creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected oral daily dosages of active compound would be 0.5 mg/kg–25 mg/kg, and preferably between 1 mg/kg–12.5 mg/kg. For parenteral administration, projected daily dosages of active compound would be 0.05 mg/kg–2.5 mg/kg, and preferably between 0.1 mg/kg—1.25 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be appropriate number of any such compositions in package form.

The standard pharmacological test procedures, which are described fully in the examples given hereafter, inter alia, demonstrate the ability of the compounds of this invention to act as antiinflammatory agents, by virtue of their ability to inhibit the activity of 5-lipoxygenase and cycloxygenase, and tetradecanoylphorbol acetam (TPA) induced ear edema.

The following examples show the preparation and pharmacological evaluation of representative compounds within the invention.

EXAMPLE 1

4-Hydroxy-3-[3-(2-oxocyclododecyl)-propionyl]-2-(5H)-furanone

A cooled solution of tetronic acid (1.05 g, 10.5 mmol) in dry methylene chloride (100 mL) was treated with triethylamine (2.32 g, 23 mmol) and 4-(dimethylamino)pyridine (0.406 g, 3.32 retool) and stirred at 0° C. for 0.5 hour. 3-(2-Oxocyclododecyl)-propionic acid (2.54 g, 10 mmol) followed by 1-(3-dimethylaminopropyl)-3-ethylcarbodiimide hydrochloride (2.02 g, 10.5 mmol) was added, and the mixture stirred at room temperature under nitrogen overnight.

The reaction was diluted with methylene chloride (300 mL) and extracted with 1N HCl (50 mL). The organic phase was washed with water (2×75 mL), dried over magnesium sulfate, and evaporated in vacuo to 2.93 g (87%) of a crude off-whim solid. Recrystallization (twice) from ethanol afforded, alter drying in vacuo at room temperature overnight, 1.5 g (45% yield) of the title compound as a homogeneous white crystalline solid, m.p. 95°–98° C. (dec).

$^1$H NMR (CDCl$_3$, 400 Mhz) δ: 11.2 (bs, 1H), 4.67 (s, 1.2H major tautomer), 4.53 (s, 0. 8H minor tautomer), 2.80-2.88 (m, 2H), 2.74 (ddd, J=17.2, 9.8, 3.3 hz, 1H), 2.63 (ddd, J=14.1, 8.3, 3.9 hz, 1H), 2.31 (ddd, J=17.2, 7.7, 3.5 hz, 1H), 2.04-2.10 (m, 1H), 1.81-1.86 (m, 1H), 1.63-1.73 (m, 3H), 1.52-1.58 (m, 1H), 1.27 (m, 14H)

$^{13}$C NMR (DMSO-d$_6$, 100 Mhz) δ: 213.33 (1C), 192.82 (1C), 188.48 (1C), 170.94 (1C), 99.19 (1C), 67.34 (1C), 5().57 (1C), 37.08 (1C), 36.26 (1C), 28.59 (1C), 25.65 (1C), 25.40 (1C), 24.74 (1C), 23.57 (1C), 22.99 (1C), 22.71 (1C), 21.85 (1C), 21.70 (1C), 21.35 (1C)

MS (EI), m/z (rel. intensity)=336 (M$^+$, 20), 195 (60), 155 (40), 127 (100) IR (KBr) v: 3430, 3080, 2950, 2880, 1750, 17(X), 1670, 1615, 1470, 1220, 1050 cm$^{-1}$ Anal. Calc'd for C$_{19}$H$_{28}$O$_5$: C, 67.83; H, 8.39

Found: C, 67.64; H, 8.22.

EXAMPLE 2

4-Hydroxy-3-[3-(2-Oxocyclododecyl)propionyl]-2-(5H)-thiophenone

A cooled solution of thiotetronic acid (0.986 g, 8.5 mmol) in dry methylene chloride (100 mL) was treated with triethylamine (1.92 g, 19 mmol) and 4-(dimethylamino)pyridine (0.32 g, 2.67 mmol) and stirred at 0° C. for 0.5 hour. 3-(2-Oxocyclododecyl)propionic acid (2.03 g, 8 mmol) followed by 1-(3-dimethylaminopropyl)-3-ethylcarbodiimide hydrochloride (1.62 g, 8.5 mmol) was added, and the mixture stirred at room temperature under nitrogen overnight.

The reaction was diluted with methylene chloride (300 mL) and extracted with 1N HCl (50 mL). The organic phase was washed with water (3×75 mL), dried over magnesium sulfate, and evaporated in vacuo to 2.47 g (88%) of a crude off-white solid. Recrystallization (twice) from ethanol afforded, after drying in vacuo at 30° C. overnight, 0.80 g (28% yield) of the title compound as a homogeneous off-white crystalline solid, m.p. 93°–95° C.

$^1$H NMR (CDCl$_3$, 400 Mhz) 8:3.97 (s, 1.6H major tautomer), 3.74 (s, 0.4H, minor tautomer), 2.87 (m, 2H), 2.71 (ddd, J=17.2, 9.8, 3.3 hz, 1H), 2.62 (bp, 1H), 2.32 (ddd, J=17.2, 8.1, 3.5 hz, 1H), 2.01 (m, 1H), 1.77 - 1.83 (m 1H), 1.62-1.71 (m, 3H), 1.54-1.61 (m, 1H), 1.27 (m, 14H)

$^{13}$C NMR (DMSO-d$_6$, 100 Mhz) 8:213.07 (1C), 197.07 (1C), 195.63 (1C), 192.54 (1C), 110.42 (1C), 50.36 (1C), 36.24 (1C), 35.59 (1C), 34.57 (1C), 28.44 ( 25.64 (1C), 25.44 (1C), 24.30 (1C), 23.53 (1C), 22.87 (1C), 22.55 (1C), 21.81 (1C), 21.42 (1C), 21.29 (1C)

MS (EI), m/z (rel. intensity)=352 (M$^+$, 20), 334 (20), 195 (55), 157 (100). 143 (70) IR (KBr)v: 3430, 2940, 2885, 1700, 1630, 1480, 1420, 1390, 1270, 1215, 1135 cm$^{-1}$ Anal. Calcd. for C$_{19}$H$_{28}$O$_4$S: C, 64.74; H, 8.01

Found: C, 64.19; H, 7.85.

EXAMPLE 3

3-{3-[2-(Benzyloxyimino)cyclododecyl]-propionyl}-4-hydroxy- 2-(5H)-furanone
2-amino-(2-hydroxymethyl)-1,3-propanediol
salt Step a)

3-(2-Oxocyclododecyl)-propionic acid, Methyl Ester

A solution of 3-(2-oxocyclododecyl)-propionic acid (7.0 g, 27.5 mmol) in methanol (80 mL) was treated with concentrated sulfuric acid (0.3 mL, 5.4 mmol) and the mixture heated under reflux for 1 hour. After concentration of the reaction mixture in vacuo the residue was diluted with ether (1.1L) and washed sequentially with saturated sodium bicarbonate (100 mL) and water (2×100 mL). The organic phase was dried over magnesium sulfate and evaporated in vacuo to a crude oil (7.1 g, 96%). Purification by flash column chromatography on silica gel (100:1 ratio) by elution with hexane/ethyl acetate (95/5) afforded 6.1 g (83% yield) of the title compound as a waxy solid on cooling, m.p. 33°–35° C.

$^1$H NMR (CDCl$_3$, 400 Mhz) δ: 3.66 (s, 3H), 2.68 (ddd, J=17.0, 9.3, 3.3 hz, 1H), 2.64 (m, 1H), 2.34 (ddd, J=17.0, 8.1, 3.5 hz, 1H), 2.26 (m, 2H), 2.00 (dq, J=13.9, 7.1 hz, 1H), 1.75-1.87 (m, 1H), 1.64 (m, 4H), 1.30 (m, 14H)

$^{13}$C NMR (CDCl$_3$, 100 Mhz) δ: 213.60 (1C), 173.54 (1C), 51.47 (1C), 50.71 (1C), 37.38 (1C), 31.81 (1C), 29.18 (1C), 25.98 (1C), 25.69 (1C), 25.60 (1C), 23.95 (1C), 23.55 (1C), 23.20 (1C), 22.15 (JC), 22.00 (1C), 21.75 (1C)

MS (CI), m/z (rel. intensity)=269 (MH$^+$, 10), 144 (70), 112 (50), 98 (80), 74 (100) IR (KBr) v: 2930, 2880, 1735, 1705, 1470, 1440, 1250, 1170 cm$^{-1}$ Anal. Calc'd. for C$_{16}$H$_{28}$O$_3$: C,71.60; H, 10.52

Found: C,71.85; H, 10.48.

Step b)

3-[2-(Benzyloxyimino)cyclododecyl]-propionic acid, Methyl Ester

A heavy walled reaction tube was charged with 3-(2-oxocyclododecyl)-propionic acid, methyl ester (6.0 g, 22.3 mmol), benzyloxyamine hydrochloride (3.99 g, 25 mmol), and pyridine (30 mL). The tube was sealed and heated in an oil bath at 140° C. for 2 hours. Upon cooling, the reaction mixture was diluted with ether (1L) and extracted with 2NN HCl until the aqueous layer was acidic, followed by extraction with water (2×50 mL). The organic phase was dried over magnesium sulfate, filtered through a silica gel plug, and the solvent removed in vacuo to afford 8.1 g (97%) of a crude oil. Purification by flash column chromatography on silica gel (100:1 ratio) and by elution with hexane/ethyl acetate (95/5) afforded 7.7 g (92% yield) of the title compound as a colorless oil with a 4:1 (E/Z) isomer ratio. $^1$H NMR (CDCl$_3$, 400 Mhz) δ: 7.23-7.36 (m, 5H), 5.03 (s, 2H, (E) major isomer), 5.02 (s, 2H, (Z) minor isomer), 3.63 (s, 2.4H, (E) major isomer), 3.61 (s, 0.6H, (Z) minor isomer), 2.63 (ddd, J=13.3, 9.8, 4.8 hz, 1H), 2.36 (m, 1H), 2.24 (m, 2H), 2.05 (m, 1H), 1.75-1.84 (m, 2H), 1.69 (m, 2H), 1.52-1.62 (m, 1H), 1.40 -1.51 (m, 1H), 1.26 (m, 14H)

$^{13}$C NMR (CDCl$_3$, 100 Mhz) 15 ((E) major isomer): 174.00 (1C), 161.48 (1C), 138.46 (1C), 128.35 (1C), 128.25 (1C), 128.08 (2H), 127.40 (1C), 75.37 (1C), 51.42 (1C), 40.87 (1C), 31.30 (1C), 30.16 (1C), 29.17 (1C), 25.93 (1C), (1C), 25.45 (1C), 24.87 (1C), 24.77 (1C), 23.83 (1C), 23.68 (1C), 22.85 (1C), 22.66 (1C)

MS (CI), m/z (rel. intensity)=374 (MH$^+$, 100), 266 (20) IR (Film) v: 2940, 2880, 1740, 1470, 1430, 700 cm$^{-1}$ Anal. Calc'd for C$_{23}$H$_{35}$NO$_3$: C, 73.96; H, 9.44; N, 3.75

Found: C, 74.24; H, 9.43: N, 3.81.

Step c)

3-[2-(Benzyloxyimino)cyclododecyl]-propionic acid

A solution of 3-[2-(benzyloxyimino)cyclododecyl]-propionic acid, methyl ester (6.68 g, 17.88 mmol) in methanol (100 mL) was treated with 2.5N sodium hydroxide (40 mL, 100 mmol) and heated under reflux for 2.5 hours. The reaction mixture was neutralized with 2N HCl (60 mL, 120 mmol) and extracted with ether (3×300 mL). The combined organic phase was washed with water (2×75 mL), dried over magnesium sulfate, and evaporated in vacuo to 6.66 g (104%) of a crude oil which crystallized on standing. Purification by recrystallization from hexane (100 mL) afforded 5.92 g (92% yield) of the free acid (2:1 (E/Z) isomer ratio) as a homogeneous white crystalline solid, m.p. 78°–80° C.

$^1$H NMR (CDCl$_3$, 400 Mhz) δ: 11.2 (bs, 1H), 7.24-7.36 (m, 5H), 5.04 (s, 2H, (E) major isomer), 5.03 (s, 2H, (Z) minor isomer), 2.61 (ddd, J=13.3, 9.5, 5.0 hz, 1H), 2.39 (m, 1H), 2.26 (m, 2H), 2.08 (m, 1H), 1.74 - 1.84 (m, 2H), 1.63-1.73 (m 2H), 1.53-1.62 (m, 1H), 1.42-1.52 (m, 1H), 1.27 (m, 14H)

$^{13}$C NMR (CDCl$_3$, 100 Mhz) δ: 179.77 (1C, (E) major isomer), 179.48 (1C, (Z) minor isomer), 161.52 (1C, (E) major isomer), 160.34 (1C, (Z) minor isomer), 138.46 (1C, (Z) minor isomer), 138.42 (1C, (E) major isomer), 128.41 (1C), 128.29 (1C), 128.13 (1C), 128.10 (1C), 127.48 (1C), 75.41 (1C), 40.94 (1C), 31.26 30.24 (1C), 28.79 (1C), 25.89 (1C), 25.79 (1C), 25.39 (1C), 24.94 (1C), 24.84 (1C), 23.85 (1C), 23.72 (1C), 22.90 (1C), 22.75 (1C)

MS (EI), m/z (rel. intensity)=359 (M$^+$, 60), 300 (20), 268 (15), 91 (100) IR (KBr) v: 3420, 2930, 2860, 1700, 1470, 1455, 1280, 1235, 1210, 985, 695 cm$^{-1}$ Anal. Calcd. for C$_{22}$H$_{33}$NO$_3$: C, 73.50; H, 9.25; N, 3.90

Found: C, 73.70; H, 9.25; N, 3.74.

Step d)

3-{3-[2-(Benzyloxyimino)cyclododecyl]-propionyl}-4-hydroxy -2-(5H)-furanone 2-amino-(2-hydroxymethyl)-1,3-propanediol salt A cooled solution of tetronic acid (0.84 g, 8.4 mmol) in dry methylene chloride (150 mL) was treated with triethylamine (1.82 g, 18 mmol) and 4-(dimethylamino)pyridine (0.325 g, 2.66 mmol) and stirred at 0° C. for 0.5 hour. 3-[2-(Benzyloxyimino)cyclododecyl] -propionic acid (2.88 g, 8 mmol) followed by 1-(3 -dimethylaminopropyl)-3-ethylcarbodiimide hydrochloride (1.61 g, 8.4 mmol) was added, and the mixture stirred at room temperature under nitrogen overnight.

The reaction was diluted with methylene chloride (500 mL) and extracted with 1N HCl (2×120 mL). The organic phase was washed with water (2×100 mL), dried over magnesium sulfate, and evaporated in vacuo to 3.22 g (91%) of a crude yellow oil.

Conversion of the oil to the tromethamine salt in ethanol-ether afforded 2.83 g (63% yield) of the title compound as a homogeneous white solid with a 2:1 (E/Z) isomer ratio, m.p. 148°–150° C.

$^1$H NMR (DMSO-d$_6$, 400 Mhz) δ: 7.66 (bs, 3H), 7.23-7.34 (m, 5H), 5.14 (bs, 3H), 4.99 (d, J=12.4 hz, 2H, (E) major isomer), 4.95 (d, J=12.4 hz, 2H, (Z) minor isomer), 3.96 (s, 2H), 3.50 (2, 6H), 1.85-2.70 (m, 5H), 0.9-1.75 (m, 20H).

$^{13}$C NMR (DMSO-d$_6$, 100 Mhz) δ: 192.88 (1C, (E) major isomer), 192.29 (1C, (E) major isomer), 192.03 (1C, (Z) minor isomer), 174.81 (1C), 161.96 (1C, (E) major isomer), 160.70 (1C, (Z) minor isomer), 138.61 (1C, (Z) minor isomer), 138.45 (1C, (E) major isomer), 128.05 (4C, (E) major isomer), 128.03 (4C, (Z) minor isomer), 127.35 (1C, (E) major isomer), 127.28 (1C, (Z) minor isomer), 94.67 (1C, (E) major isomer), 94.56 (1C, (Z) minor isomer), 74.53 (1C, (E) major isomer), 74.49 (1C, (Z) minor isomer), 68.95 (1C), 60.99 (1C), 59.31 (3C), 40.54 (1C), 37.67 (1C), 30.16 (1C), 29.73 (1C), 25.91 (1C), 25.71 (1C), 25.55 (1C), 24.30 (1C), 24.21 (1C), 23.51 (1C), 23.36 (1C), 22.40 (1C), 21.94 (1C)

MS (EI), m/z (rel. intensity)=441 (M$^+$, 10), 359 (10), 30) (10), 240 (20), 90 (100) IR (KBr)v: 3400, 3060, 2920, 1710, 1640, 1595, 1520, 1450, 1040, 1015, 935, 700 cm$^{-1}$ Anal. Calc'd for C$_{26}$H$_{35}$NO$_5$·C$_4$H$_{11}$NO$_3$: C, 64.04; H, 8.24; N, 4.98

Found: C, 64.28; H, 8.28; N, 4.90.

EXAMPLE 4

3-{3-[2-(Benzyloxyimino)cyclododecyl]-propionyl}-4-hydroxy- 2-(5H)-thiophenone 2-amino-(2-hydroxymethyl)-1,3-propanediol salt A cooled solution of thiotetronic acid (0.97 g, 8.4 mmol) in dry methylene chloride (150 mL) was treated with triethylamine (1.82 g, 18 mmol) and 4-(dimethylamino)pyridine (0.325 g, 2.66 mmol) and stirred at 0° C. for 0.5 hour. 3-[2-(Benzyloxyimino)cyclododecyl] -propionic acid (2.88 g, 8 mmol) followed by 1-(3 -dimethylaminopropyl)-3-ethylcarbodiimide hydrochloride (1.61 g, 8.4 mmol) was added, and the mixture stirred at room temperature under nitrogen overnight.

The reaction was diluted with methylene chloride (500 mL) and extracted with 1N HCl (2×120 mL). The organic phase was washed with water (2×100 mL), dried over magnesium sulfate, and evaporated in vacuo to 3.32 g (91%) of a crude yellow oil.

Conversion of the oil to the tromethamine salt in ethanol-ether afforded 2.00 g (43% yield) of the title compound as a homogeneous white solid, m.p. 126°–128° C.

$^1$H NMR (DMSO-d$_6$, 400 Mhz) δ: 7.65 (bs, 3H), 7.23-7.34 (m, 5H), 5.14 (bs, 3H), 4.99 (d, J=12.4 hz, 2H, (E) major isomer), 4.95 (d, J=12.7 hz, 2H, (Z) minor isomer), 3.50 (s, 6H), 3.30 (2, 2H), 1.85-2.70 (m, 5H), 0.9-1.75 (m, 20H).

$^{13}$C NMR (DMSO-d$_6$, 100 Mhz) δ: 194.81 (1C, (E) major isomer), 194.78 (1C, (E) major isomer), 192.51 (1C, (E) major isomer), 192.29 (1C, (Z) minor isomer), 192.28 (1C, (Z) minor isomer), 192.21 (1C, (Z) minor isomer), 161.96 (1C, (E) major isomer), 160.70 (1C, (Z) minor isomer), 138.58 (1C, (Z) minor isomer), 138.43 (1C, (E) major isomer), 128.02 (4C, (Z) minor isomer), 128.00 (4C, (E) major isomer), 127.98 (1C, (E) major isomer), 127.24 (1C, (Z) minor isomer), 106.42 (1C, (E) major isomer), 1()6.31 (1C, (Z) minor isomer), 74.49 (1C, (E) major isomer), 74.45

(1C, (Z) minor isomer), 60.95 (1C), 59.30 (3C), 40.50 (1C), 38.06 (1C), 36.51 (1C), 30.15 (1C). 29.73 (1C), 25.88 (1C), 25.68 (1C), 25.52 (1C), 24.28 (1C), 24.18 (1C), 23.47 (1C), 23.35 (1C), 22.37 (1C), 21.92 (1C)

MS (EI), m/z (rel. intensity)=457 ($M^+$, 4), 3(i4) (4), 90 (100), 60 (80) IR (KBr)v: 3420, 3200, 2930, 2850, 1645, 1605, 1580, 1510, 1410, 1390, 1060, 890, 695 $cm^-$ Anal. Calcd. for $C_{26}H_{35}N_4S \cdot C_4H_{11}NO_3$: C, 62.26; H, 8.01; N, 4.84

Found: C, 62.20; H, 8.07; N, 4.80.

EXAMPLE 5

The ability of the compounds of the invention to act as inhibitors of the enzymes 5-lipoxygenase and cyclooxygenase was evaluated in the resident murine peritoneal macrophage standard pharmacological test procedure. This test procedure was carried out as follows.

Resident peritoneal macrophages were collected from female Swiss Webster mice (49 days old, 20–25 gms, Buckshire) by lavaging with 7–8 ml Hanks Balanced Salt Solution (HBSS) without $Ca^{++}$ and $Mg^{++}$ (GIBCO). The lavage fluid from several mice was pooled and centrifuged at 4° C. for 10 minutes at 400 xg. The cell pellet was resuspended in Medium 199 (GIBCO) with HEPES buffer containing 100 µg/ml gentamicin. Two ml of the cell suspension ($4 \times 10^6$ cells) were then plated on 35 mm culture dishes (Nunc).

A macrophage monolayer was established after a 1–1.5 hour incubation of the cells at 37° C. in an atmosphere of 95% $O_2$ and 5% $CO_2$. The monolayers were washed 2x with 2 ml HBDSS, containing $Ca^{++}$ and $Mg^{++}$ after which 2 ml Medium 199 supplemented with 10% freshly thawed heat-inactivated fetal bovine serum and 100 µg/ml gentamicin was added for an overnight incubation.

Residual serum and cellular debris were removed from the monolayers by washing 3x with 2 ml HBSS containing $Ca^{++}$ and $Mg^{++}$. Macrophages were preincubated for 5 minutes with 1 ml serum-free M199 containing 10 µl dimethyl sulfoxide (DMSO) vehicle or test compound prior to cell activation with zymosan (100 Mg/ml) or arachidonic acid (AA) (2 µM). After 2 hours, the supernatants are removed and either assayed for $LTC_4$ and $PGE_2$ by radioimmunoassay (RIA) directly or stored at −20° C. In all cases, results are expressed as ng metabolite/$4 \times 10^6$ cells.

Summary of RIAs used for quantitation of metabolite levels in zymosan or arachidonic acid stimulated mouse macrophage culture media.

| Metabolite | Range of detection (µg/ml) | Metabolite Levels (ng/4 × 10⁶cells) (x ± S.E.M.,n) |
|---|---|---|
| $LTC_4$ | 0.25–16 | 93.7 ± 9.9 (34) |
| $PGE_2$ | 0.027–20 | 30.90 ± 1.93 (39) |

Calculations: The raw data were converted to ng metabolite/$4-10^6$ cells using a standard curve. Results were then expressed as percent inhibition of zymosan induced, leukotriene or prostaglandin synthesis (control) using the following equation:

REFERENCE COMPOUNDS:
The compounds used are listed below.
$IC_{50}$ values of reference 5-lipoxygenase and/or cyclooxygenase inhibitors.

| | $IC_{50}$ µM (95%) Confidence limits | |
|---|---|---|
| Compound | $LTC_4$ | $PGE_2$ |
| BW 755c | 0.21 | 1.04 |
| | (0.10, 0.42) | (0.73, 1.49) |
| ETYA | 0.44 | 1.26 |
| | (0.36, 0.53) | (0.99, 1.60) |
| Indomethacin | >50 | 0.002 |
| | | (0.001, 0.003) |
| NDGA | 1.87 | 2.15 |
| | (0.22, 15.57) | (1.15, 4.04) |

REFERENCE COMPOUNDS:
The compounds used are listed below.
$IC_{50}$ values of reference 5-lipoxygenase and/or cyclooxygenase inhibitors.

| | $IC_{50}$ µM (95%) Confidence limits | |
|---|---|---|
| Compound | $LTC_4$ | $PGE_2$ |
| BW 755c | 0.21 | 1.04 |
| | (0.10, 0.42) | (0.73, 1.49) |
| ETYA | 0.44 | 1.26 |
| | (0.36, 0.53) | (0.99, 1.60) |
| Indomethacin | >50 | 0.002 |
| | | (0.001, 0.003) |
| NDGA | 1.87 | 2.15 |
| | (0.22, 15.57) | (1.15, 4.04) |

When tested in this standard pharmacological test procedure, representative compounds of this invention exhibited the following levels of enzyme inhibition:

TABLE I

| Compound of | $LTC_4$ | | $PGE_2$ | |
|---|---|---|---|---|
| Example No. | Dose µM | % Inhibition | Dose µM | % Inhibition |
| 1 | 0.1 | 2.1 | 0.1 | −17.9 |
|   | 0.5 | 38.7 | 0.5 | 5.8 |
| 2 | 0.1 | −4.9 | 0.1 | −35.0 |
|   | 0.5 | 39.5 | 0.5 | 3.3 |
| 3 | 0.03 | 40 | 0.03 | 8 |
|   | 0.1 | 38 | 0.1 | 58 |
|   | 0.1 | 53 | 0.1 | 6 |
|   | 0.5 | 64 | 0.5 | 86 |
|   | 0.5 | 68 | 0.5 | 59 |
| 4 | 0.03 | 45 | 0.03 | 18 |
|   | 0.1 | 37 | 0.1 | 42 |
|   | 0.1 | 66 | 0.1 | 20 |
|   | 0.35 | 97 | 0.35 | 52 |
|   | 0.5 | 77 | 0.5 | 82 |

The results obtained in this standard pharmacological test procedure showed that the compounds of this invention inhibited 5-lipoxygenase and cycloxygenase, and are therefore useful as antiinflammatory agents.

EXAMPLE 6

Representative compounds of this invention were evaluated in an in vivo standard pharmacological test procedure that measured the effect of the representative compounds on dermal inflammation, as measured by the prevention of tetradecanoylphorbol acetate (TPA) induced ear edema in Webster mice. This test procedure was carried out as follows.

Mice were placed into plastic boxes in groups of six. Eight groups of mice received TPA topically on the right ear. TPA was dissolved in acetone at a concentration of 100 ug/ml. TPA was applied to the right ear by the means of an automatic pipette. Volumes of 10 ul were applied to the inner and outer surfaces of the ear. Each mouse received 2 ug/ear TPA. The left ear (control) received acetone delivered in the same manner. The compounds to be evaluated were given orally 30 min alter treatment with TPA.

Measurements were taken with Oditest calipers, 0–10 mm with 0.01 graduations. The right and left ears were measured 4 hrs after TPA-induced inflammation.

The difference between right and left ear thickness was calculated and the significance was determined by a one way analysis of variance with Dunnet's comparisons to control (P=0.05). Drug effects are expressed as a percent change from control values according to the following formula.

$$\% \text{ change from control} = \frac{(\text{Rt. ear} - \text{Lt. ear})\text{drug} - (\text{Rt. ear} - \text{Lt. ear})\text{control}}{(\text{Rt. ear} - \text{Lt. ear})\text{control}} \times 100$$

In this test procedure, BW755c has an oral $ED_{50}$ of 88 mg/kg, phenidone has an oral $ED_{50}$ of 235 mg/kg, and indomethacin is inactive at 10 mg/g. The following results were obtained for representative compounds of this invention. At a dose of 100 mg/kg, the compounds of Examples 2, 3, and 4, inhibited TPA induced ear edema by 40, 34, and 19 percent, respectively.

These results show that the compounds of this invention prevented dermal inflammation in response to an inflammatory challenge, and are therefore useful as antiinflammatory agents.

What is claimed is:

1. A compound having the formula

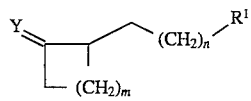

wherein $R^1$ is

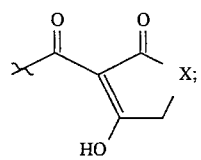

X is O, or S;

Y is O or $NOR^2$;

$R^2$ is alkyl of 1–6 carbon atoms, alkenyl of 2–7 carbon atoms, phenyl, —$CH_2CO_2R^3$, —$CH_2Ph$, —$CH_2C_6F_5$, or

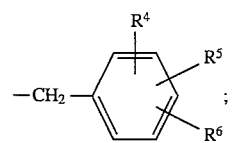

$R^3$ is hydrogen, alkyl of 1–6 carbon atoms, phenyl, or phenylalkyl of 7–12 carbon atoms;

$R^4$, $R^5$, and $R^6$ are each, independently, hydrogen, alkyl of 1–6 carbon atoms, —OH, alkoxy of 1–6 carbon atoms, —$CO_2R^3$, halogen, —$NH_2$, alkylamino of 1–6 carbon atoms, dialkylamino of 2–12 carbon atoms, or —$NO_2$;

m=0–20; and n=0–10 or a pharmacologically acceptable salt thereof.

2. The compound of claim 1 wherein m=7–12 and n=0–2 or a pharmaceutically acceptable salt thereof.

3. The compound of claim 1, which is 4-hydroxy-3-[3-(2-oxocyclododecyl)-propionyl]-2-(5H)-furanone or a pharmaceutically acceptable salt thereof.

4. The compound of claim 1, which is 4-hydroxy-3-[3-(2-oxocyclododecyl) propionyl]-2-(5H)-thiophenone or a pharmaceutically acceptable salt thereof.

5. The compound of claim 1, which is 3-{3-[2-(benzyloxyimino)cyclododecyl]-propionyl}-4-hydroxy-2-(5H)-furanone 2-amino-(2-hydroxymethyl)-1,3-propanediol salt.

6. The compound of claim 1 which is 3-{3-[2-(benzyloxyimino)cyclododecyl]-propionyl}-4-hydroxy-2-(5H)-thiophenone 2-amino-(2-hydroxymethyl)-1,3propanediol salt.

7. A method of treating an inflammatory condition in a mammal which comprising to said mammal an antiinflammatory effective amount of a compound having the formula

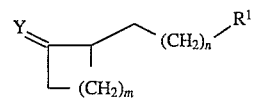

wherein $R^1$ is

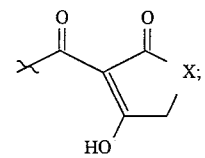

X is O, or S;

Y is O or $NOR^2$;

$R^2$ is alkyl of 1–6 carbon atoms, alkenyl of 2–7 carbon atoms, phenyl, —$CH_2CO_2R^3$, —$CH_2Ph$, —$CH_2C_6F_5$, or

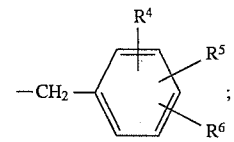

$R^3$ is hydrogen, alkyl of 1–6 carbon atoms, phenyl, or phenylalkyl of 7–12 carbon atoms;

$R^4$, $R^5$, and $R^6$ are each, independently, hydrogen, alkyl of 1–6 carbon atoms, —OH, alkoxy of 1–6 carbon atoms, —$CO_2R^3$, halogen, —$NH_2$, alkylamino of 1–6 carbon atoms, dialkylamino of 2–12 carbon atoms, or —$NO_2$;

m=0–20; and n=0–10 or a pharmacologically acceptable salt thereof.

8. A pharmaceutical composition which comprises a compound having the formula

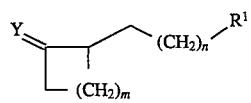

wherein

R¹ is

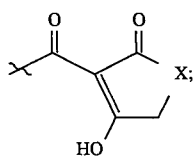

X is O, or S;

Y is O or NOR²;

R² is alkyl of 1-6 carbon atoms, alkenyl of 2-7 carbon atoms, phenyl, —CH₂CO₂R³, —CH₂Ph, —CH₂C₆F₅, or

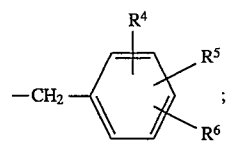

R³ is hydrogen, alkyl of 1-6 carbon atoms, phenyl, or phenylalkyl of 7-12 carbon atoms;

R⁴, R⁵, and R⁶ are each, independently, hydrogen, alkyl of 1-6 carbon atoms, —OH, alkoxy of 1-6 carbon atoms, —CO₂R³, halogen, —NH₂, alkylamino of 1-6 carbon atoms, dialkylamino of 2-12 carbon atoms, or —NO₂;

m=0-20; and n=0-10 or a pharmacologically acceptable salt thereof, and a pharmaceutical carrier.

* * * * *